(12) United States Patent
Sidhu (10) Patent No.: US 11,131,734 B2
(45) Date of Patent: Sep. 28, 2021

(54) PROCESSING MULTIDIMENSIONAL SIGNALS

(71) Applicant: Gagan Sidhu, Edmonton (CA)

(72) Inventor: Gagan Sidhu, Edmonton (CA)

(*) Notice: Subject to any disclaimer, the term of this patent is extended or adjusted under 35 U.S.C. 154(b) by 456 days.

(21) Appl. No.: 14/651,930

(22) PCT Filed: Dec. 12, 2013

(86) PCT No.: PCT/CA2013/001033
§ 371 (c)(1),
(2) Date: Jun. 12, 2015

(87) PCT Pub. No.: WO2014/089684
PCT Pub. Date: Jun. 19, 2014

(65) Prior Publication Data
US 2015/0316632 A1   Nov. 5, 2015

Related U.S. Application Data

(60) Provisional application No. 61/737,032, filed on Dec. 13, 2012.

(51) Int. Cl.
*G01R 33/54* (2006.01)
*G01N 33/49* (2006.01)
(Continued)

(52) U.S. Cl.
CPC .............. *G01R 33/54* (2013.01); *A61B 5/055* (2013.01); *G01N 33/4925* (2013.01); *A61B 5/14542* (2013.01); *A61B 2576/026* (2013.01)

(58) Field of Classification Search
CPC .............. G01R 33/54; G01R 33/56341; G01N 33/4925; A61B 5/055; A61B 5/0263;
(Continued)

(56) References Cited

U.S. PATENT DOCUMENTS 7,089,217 B2   8/2006   Kasabov
7,877,342 B2   1/2011   Buscema
(Continued)

FOREIGN PATENT DOCUMENTS

GB      2 438 461 A        11/2007
WO      WO2014089684   *   6/2014

OTHER PUBLICATIONS

Logothetis; "What we can do and what we cannot do with fMRI"; Nature; Jun. 12, 2008; pp. 869-878; vol. 453; Macmillan Publishers Limited.
(Continued)

*Primary Examiner* — Michael P Nghiem
(74) *Attorney, Agent, or Firm* — Hoffberg & Associates; Steven M. Hoffberg; Steven M Hoffberg (57) ABSTRACT

A computer-implemented method, computing system and non-transitory computer readable medium having computer readable code thereon for processing a dataset of multidimensional signals captured from points in a physical space. The computer-implemented method includes using a computing system, determining, for each of the points, a plurality of spatially neighbouring points in the physical space; and using the computing system, creating a modified signal for each point based on the signals of its respective spatially neighbouring points.

21 Claims, 8 Drawing Sheets

(51) Int. Cl.
  *A61B 5/055* (2006.01)
  *A61B 5/145* (2006.01)

(58) Field of Classification Search
  CPC ....... A61L 35/055; G06T 7/0016; G06T 7/30; G06T 5/002
  USPC ........................................................ 702/189
  See application file for complete search history.

(56) References Cited

U.S. PATENT DOCUMENTS

| | | | | |
|---|---|---|---|---|
| 2002/0167518 | A1* | 11/2002 | Migdal | G06T 17/20 345/428 |
| 2007/0233624 | A1 | 10/2007 | Buscema | |
| 2008/0247668 | A1* | 10/2008 | Li | G06K 9/32 382/285 |
| 2009/0324040 | A1 | 12/2009 | Lindop et al. | |
| 2010/0286500 | A1* | 11/2010 | Ruhm | G01R 33/4824 600/410 |
| 2011/0051832 | A1* | 3/2011 | Mergen | H04L 1/06 375/267 |
| 2011/0075903 | A1 | 3/2011 | Martinez | |
| 2013/0182932 | A1* | 7/2013 | Chen | G01R 33/56509 382/131 |
| 2013/0322728 | A1* | 12/2013 | Jacobs | A61B 5/055 382/132 |
| 2014/0071347 | A1* | 3/2014 | Chen | H04N 1/6008 348/576 |
| 2015/0323628 | A1* | 11/2015 | Wald | G01R 33/341 324/309 |
| 2016/0171695 | A1* | 6/2016 | Jacobs | A61B 5/055 382/131 |

OTHER PUBLICATIONS

Herbrich; "Learning Kernel Classifiers: Theory and Algorithms"; pp. 37-38; 2002; MIT Press.
Rudin; "Functional Analysis, Second Edition"; 1991; p. 3; McGraw-Hill Book Co.
Khuri; "Basic Concepts in Linear Algebra", Chapter 2; Advanced Calculus with Applications in Statistics, Second Edition; 2003; John Wiley & Sons, Inc.
Feller; "Introduction to Probability Theory and Its Applications"; pp. 229-233; Third Edition; 2008; Wiley.
Saul et al., "An Introduction to Locally Linear Embedding", AT&T Labs—Research, 2000, Florham Park, NJ, U.S.A.
Saul et al., "Think Globally, Fit Locally: Unsupervised Learning of Low Dimensional Manifolds", Journal of Machine Learning Research 4, (2003), 119-155.

* cited by examiner

Fig. 1A

Copyright 2012 Gagan Sidhu

Fig. 1B
Copyright 2012 Ganan Sidhu

Fig. 2
Copyright 2012 Ganan Sidhu

Fig. 6
Copyright 2012 Ganan Sidhu

Fig. 7

PROCESSING MULTIDIMENSIONAL SIGNALS

FIELD OF THE INVENTION

COPYRIGHT NOTICE

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

The following relates generally to signal processing, and more particularly to a computer-implemented method, a computing system, and a computer program product for processing multidimensional signals captured from physical space.

BACKGROUND OF THE INVENTION

Raw multidimensional signals may be captured from physical space by various devices, using various techniques, and for various uses. In the field of data processing, it is often a goal to process raw multidimensional signals in order to obtain representations of the signals that are more useful than when in raw form, for subsequent processing and other operations such as classification, visualization and the like.

Various techniques for processing multidimensional signals in an attempt to obtain more useful representations through reconstruction, for example by way of dimensionality reduction, include the well-understood principle component analysis (PCA) and multidimensional scaling (MDS) techniques. Each of PCA and MDS are eigenvector techniques that are useful for modeling linear variabilities in raw multidimensional data.

For modelling nonlinear variabilities in raw multidimensional data, the unsupervised technique of local linear embedding (LLE) has been found to be useful. LLE was described by Sam Roweis and Lawrence Saul in their paper entitled "Nonlinear dimensionality reduction by locally linear embedding" (Science, v. 290 no. 5500, December 2000, pp. 2323-2326). According to this technique, nonlinear manifolds in the raw multidimensional data may first be modeled as locally-linear patches, which patches are then preserved in the reconstruction such that neighbours remain neighbours after reconstruction. A technique for dealing with what can be highly nonlinear embeddings resulting from LLE was subsequent described by Roweis and Saul in their paper entitled "Think Globally, Fit Locally: Unsupervised Learning of Nonlinear Manifolds" (Technical Report MS CIS-o2-18, University of Pennsylvania Scholarly Commons, 2003).

An example of a raw multidimensional signal is a blood oxygenation level dependent (BOLD) signal captured from each of multiple points within physical space (in this example a three-dimensional volume) using functional magnetic resonance imaging (fMRI). The physical space may contain the brain of a subject, and the fMRI devices use paramagnetic deoxyhemoglobin within the brain as a BOLD contrast. That is, a BOLD intensity signal for a given point in the physical space can represents the oxygenation over time of the blood at that point, which in turn can indicate the oxygen-dependent neuronal activity at that point. Being able to capture data indicating neuronal activity at a given point in a brain can be very useful for studying brain activity and diseases.

It is known to process fMRI BOLD signal data using LLE. For example, Mannfolk et al., in "Dimensionality Reduction of fMRI Time Series Data Using Locally Linear Embedding" (Magnetic Resonance Material Physics, Mar. 13, 2010, Volume 23; Pages 432-338) disclose that, for non-linear example data, LLE, unlike PCA, can separate non-linearly modulated sources in a low-dimensional subspace, and that LLE can also perform better than non-linear PCA.

However, the above-referenced technique for processing fMRI BOLD signal data using LLE undertakes a neighbourhood selection step that essentially establishes locality based on similarities between fMRI signals across the dataset. Because of this, reconstructions of different patients' fMRI datasets could use fMRI signals from non-corresponding spatial points in the physical space (i.e. the three-dimensional volumes containing the respective brains) being assessed.

With fMRI signals, since the spatial information is lost during the reconstruction, hemodynamic activity at a spatial position within one subject's reconstruction cannot validly be compared to hemodynamic activity at the same spatial position within another subject's reconstruction. Because of this, there remain difficulties with identifying differences in mental activity between the subjects, and with conducting classification or other subsequent operations based on the respective reconstructions.

SUMMARY OF THE INVENTION

In accordance with an aspect, there is provided a computer-implemented method for processing a dataset of multidimensional signals captured from points in a physical space, the method comprising using a computing system, determining, for each of the points, a plurality of spatially neighbouring points in the physical space; and using the computing system, creating a modified signal for each point based on the signals of its respective spatially neighbouring points.

By creating modified signals based on signals of spatially neighbouring points, the resultant modified signals can be more easily compared across subject datasets on the basis that all subjects' reconstructed signals at a given point were reconstructed on the basis of signals from the same spatially neighbouring points in the respective datasets.

In embodiments, the dataset of multidimensional signals is a dataset of functional Magnetic Resonance Imaging (fMRI) BOLD (Blood Oxygenation Level Dependent) signals.

In accordance with another aspect, there is provided a computer-implemented method for processing a dataset of multidimensional signals captured from points in a physical space, the method comprising using a computing system, determining, for each of the points, a plurality of spatially neighbouring points in the physical space; using the computing system, creating a modified signal for each point based on the signals of its respective spatially neighbouring points.

In accordance with another aspect, there is provided a non-transitory computer readable medium embodying a computer program executable on a computing system for processing a dataset of multidimensional signals captured from points in a physical space, the computer program comprising computer program code for determining, for each of the points, a plurality of spatially neighbouring points in the physical space; and computer program code for creating a modified signal for each point based on the signals of its respective spatially neighbouring points.

In accordance with another aspect, there is provided a computing system comprising at least one processor executing instructions for processing a dataset of multidimensional signals captured from points in a physical space, the at least one processor configured therewith to determine, for each of the points, a plurality of spatially neighbouring points in the physical space; and create a modified signal for each point based on the signals of its respective spatially neighbouring points.

In accordance with another aspect, there is provided a computer-implemented method for processing a dataset of multidimensional signals captured from points in a physical space, the method comprising conducting local linear embedding on the dataset, wherein reconstruction weights for the signal at each point are established using signals at spatially neighbouring points that are within a spatial neighbourhood of the point in the physical space.

In accordance with another aspect, there is provided a computer-implemented method for processing a dataset of multidimensional signals captured from points in a physical space, the method comprising determining reconstruction weights for the signal at each point based on signals at spatially neighbouring points that are within a spatial neighbourhood of the point in the physical space; and constructing modified signals using local linear embedding based on the reconstruction weights.

In accordance with another aspect, there is provided a computing system comprising at least one processor executing instructions for processing a dataset of multidimensional signals captured from points in a physical space, the at least one processor configured therewith to conduct local linear embedding on the dataset, wherein reconstruction weights for the signal at each point are established using signals at spatially neighbouring points that are within a spatial neighbourhood of the point in the physical space.

BRIEF DESCRIPTION OF THE DRAWINGS

Embodiments of the invention will now be described with reference to the appended drawings in which.

DETAILED DESCRIPTION

The description of the invention to follow is, for ease of understanding, made in connection with an embodiment where the dataset of multidimensional signals is a dataset of functional Magnetic Resonance Imaging (fMRI) BOLD (Blood Oxygenation Level Dependent) signals. However, it will be understood that the invention is applicable to the processing of datasets of other kinds of multidimensional signals captured from points in a physical space, such as other spatiotemporal signals, of which fMRI BOLD signals are an example.

A local interpretation of fMRI data may be expressed in terms of a BOLD signal comprising BOLD intensity values over T time points (T being greater than or equal to 1) being a T-dimensional spatial pattern observed at the spatial point in the physical space being assessed, as defined by the respective point of the voxel in the fMRI data.

A global interpretation of fMRI data may be expressed in terms of the fMRI data containing T uniformly-spaced time points, where time point $t \in \{1, \ldots, T\}$ references a physical space that is a three-dimensional volume comprised of $V = L \times W \times H$ points, or voxels (volumetric elements), having a respective BOLD intensity value. That is, each voxel is a volumetric measurement of the brain's physical mechanisms in both space and time. The measurement may be expressed as four-tuple (x, y, z, t).

The local interpretation may be employed to determine the mathematical structures of the local configurations of the fMRI data in space-time, whereas the global interpretation may be employed to perform a global optimization that conserves the mathematical structure of the local configurations. A topological space that represents the physical reality must satisfy both the local and global interpretations.

Figure 1A:
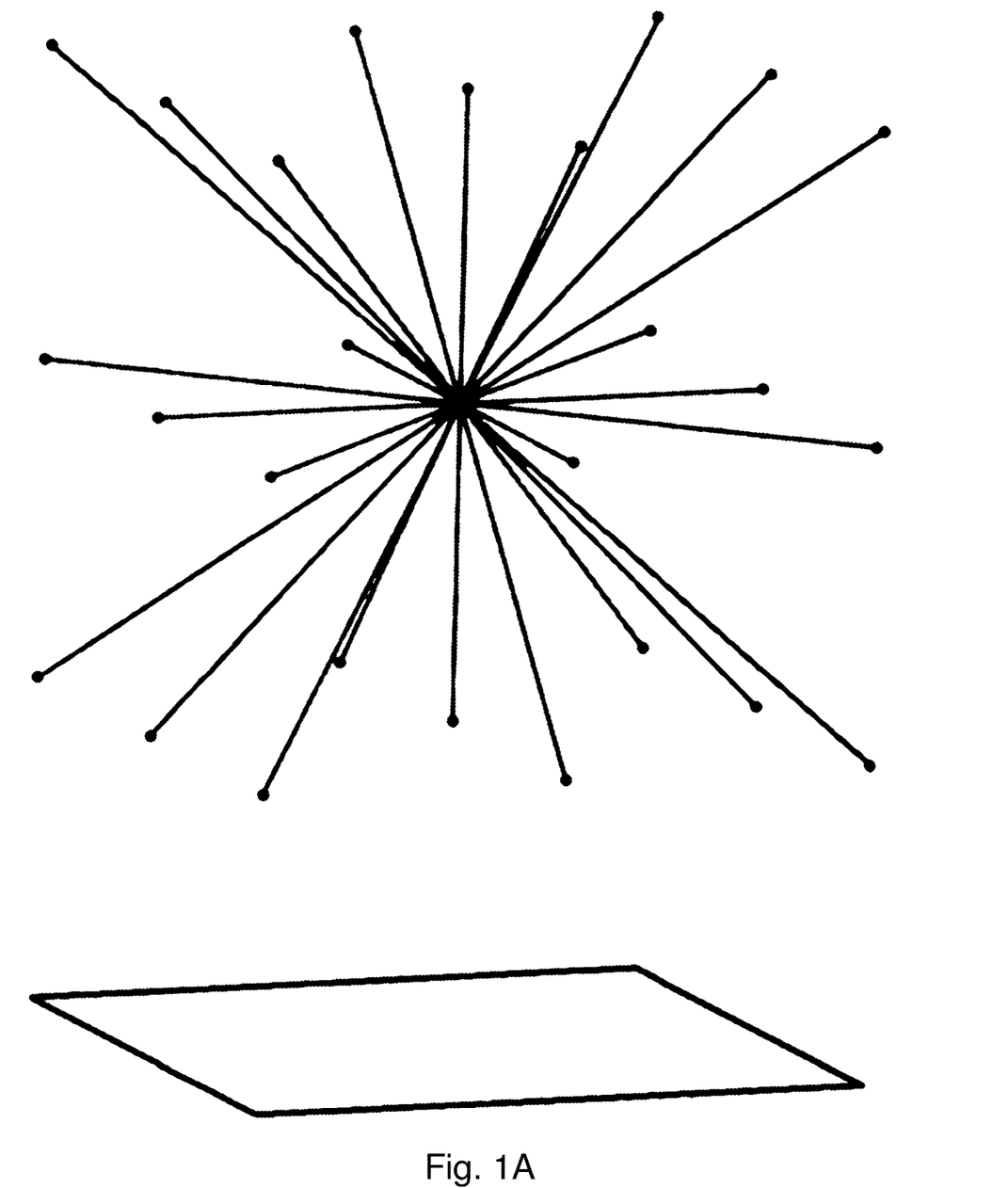
FIG. 1A is a graphical depiction of a voxel modelled as a black body in a three-dimensional Cartesian physical space, along with spatially neighbouring voxels.

FIG. 1A is a graphical depiction of a voxel modelled as a black body in a three-dimensional Cartesian physical space, along with a number (K) of its spatially neighbouring voxels within a neighbourhood. The set containing the spatial coordinates of all voxels in the three-dimensional Cartesian physical space may be represented as in Equation 1, below:

$$X = \{(x,y,z): x \in \{1, \ldots, L\}, y \in \{1, \ldots, W\}, z \in \{1, \ldots, H\}\} \quad (1)$$

Figure 1B:
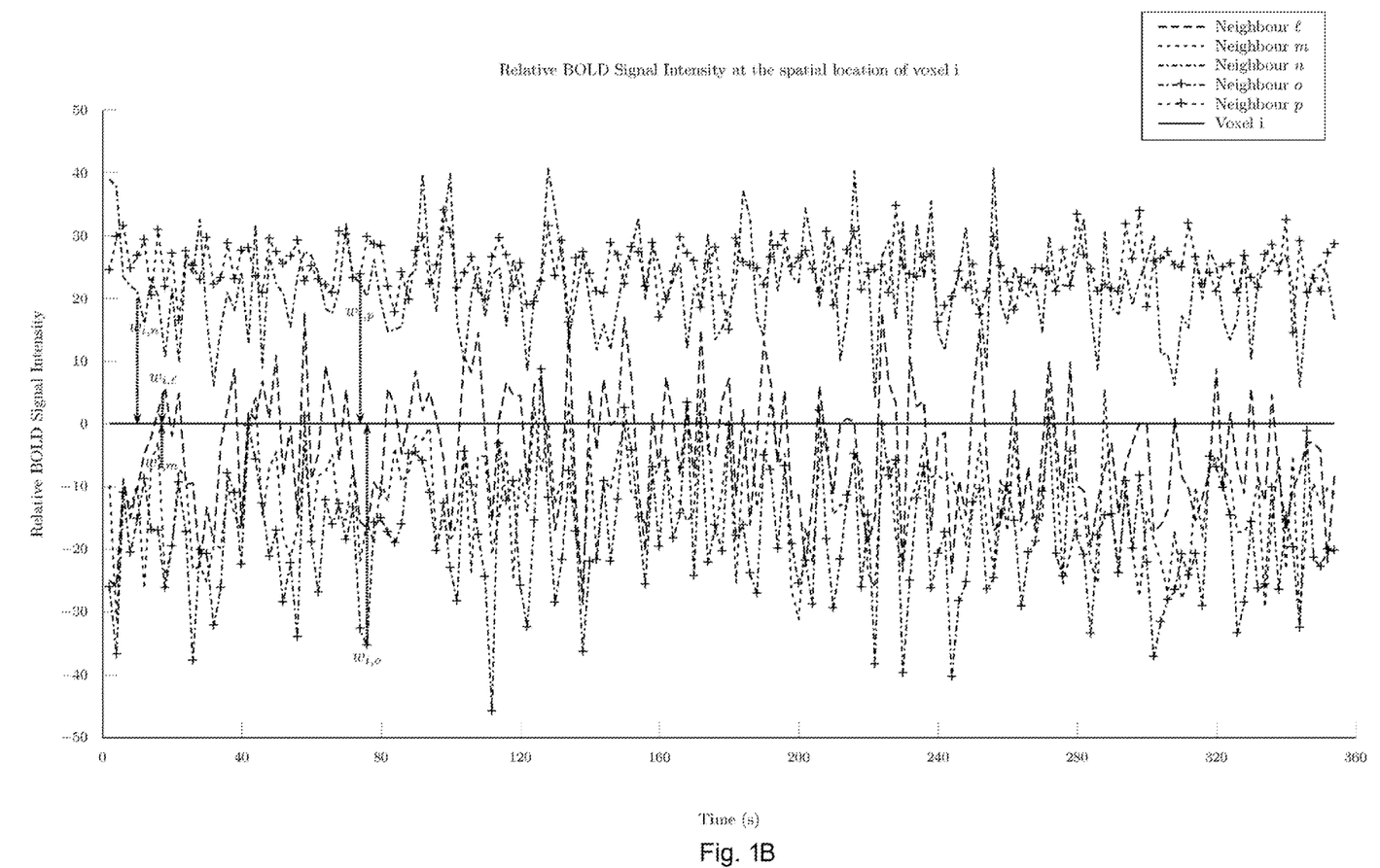
FIG. 1B is a plot of the relative fMRI BOLD signal intensities of spatially neighbouring points relative to the origin representing the black body relative to its spatial neighbours.

FIG. 1B is a plot of the relative fMRI BOLD signal intensities of spatially neighbouring points relative to the origin line at zero, representing the black body relative to its spatial neighbours.

Figure 2:
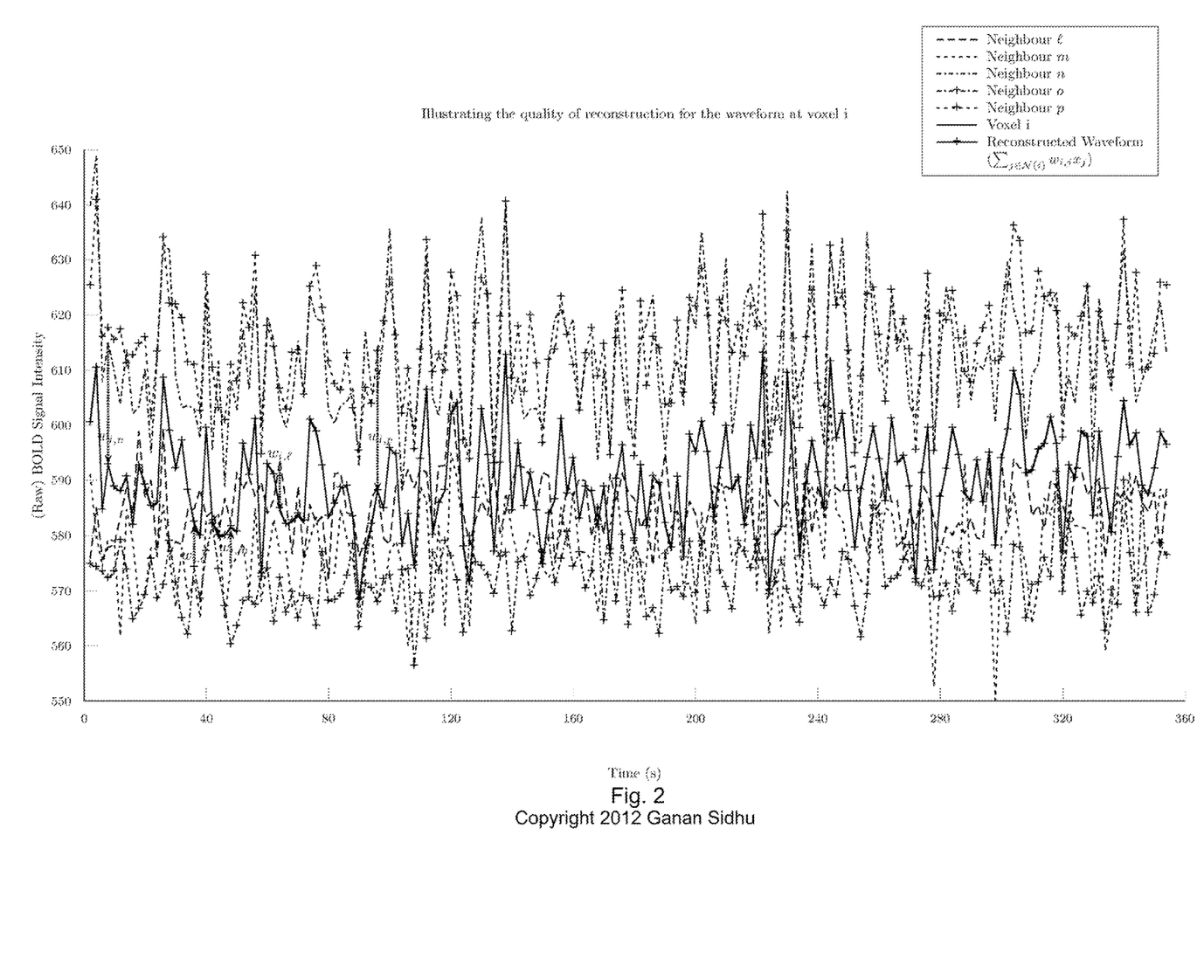
FIG. 2 is a plot of a subset of a raw fMRI dataset and an fMRI signal reconstructed according to the invention disclosed herein.

FIG. 2 is a plot of a subset of an fMRI dataset with raw, or original, captured BOLD signal intensities of spatially neighbouring points relative to the BOLD signal intensity of a selected point, over the assessment time period. FIG. 2 also shows the reconstructed fMRI signal of the point based on the fMRI signals of these spatially neighbouring points.

Figure 3:
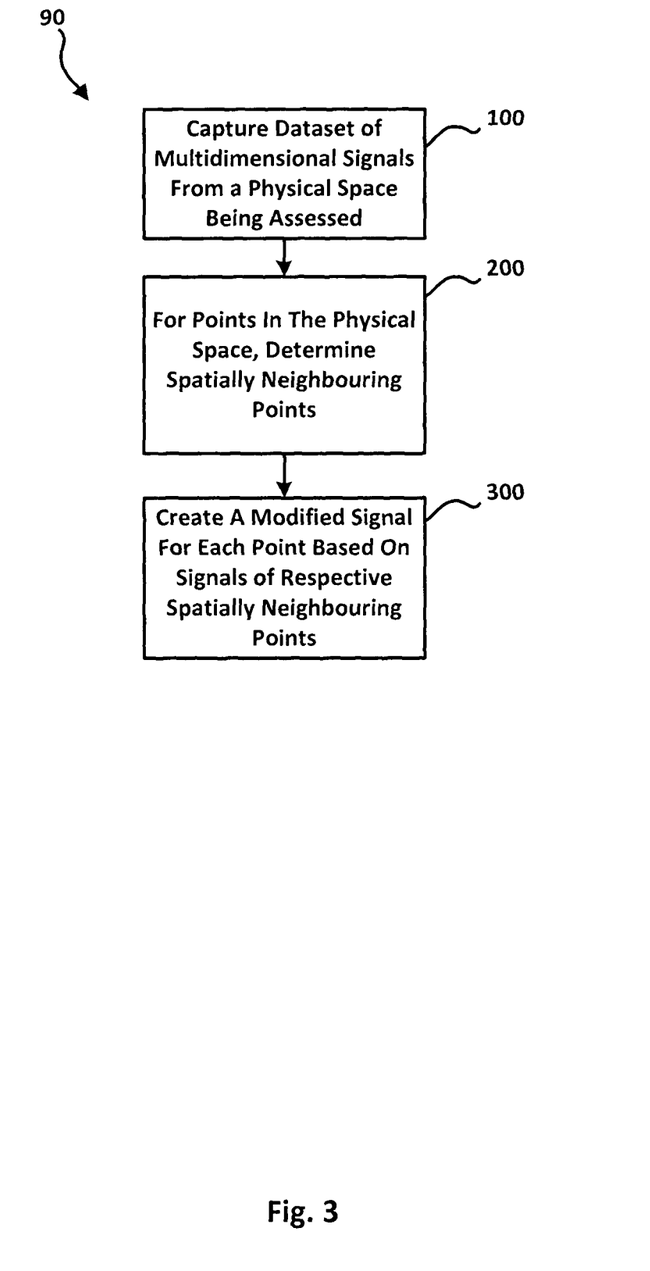
FIG. 3 is a flowchart depicting the general steps for processing a dataset of fMRI signals, according to an embodiment.

FIG. 3 is a flowchart depicting the general steps in a computer-implemented method 90 for processing a dataset of multidimensional signals captured from points in a physical space, according to an embodiment where the multidimensional signals are fMRI BOLD signals captured from points in a three-dimensional volume. Initially, a dataset of the fMRI BOLD signals is captured from the three-dimensional (3D) volume being assessed (step 100). The dataset may captured and formatted according to the NIFTI (Neuroimaging Informatics Technology Initiative) file format, where each BOLD measurement at each time point t and at each spatial point (x, y, z) in the three-dimensional volume being assessed is expressed as a four-tuple (x, y, z, t). The dataset may be represented in a single file, or in a set of multiple files.

The dataset is then processed to mask out the points that do not represent points in the three-dimensional volume being assessed that are coincident with the brain. The points that are masked out will not have any fMRI BOLD signal measurements. The dataset is then further processed to determine spatially neighbouring points within a spatial neighbourhood of each point in the three-dimensional volume (step 200). With the spatially neighbouring points for each point having been determined, a modified fMRI BOLD signal for each point is then created based on the fMRI BOLD signals of its spatially neighbouring points (step 300).

Figure 4:
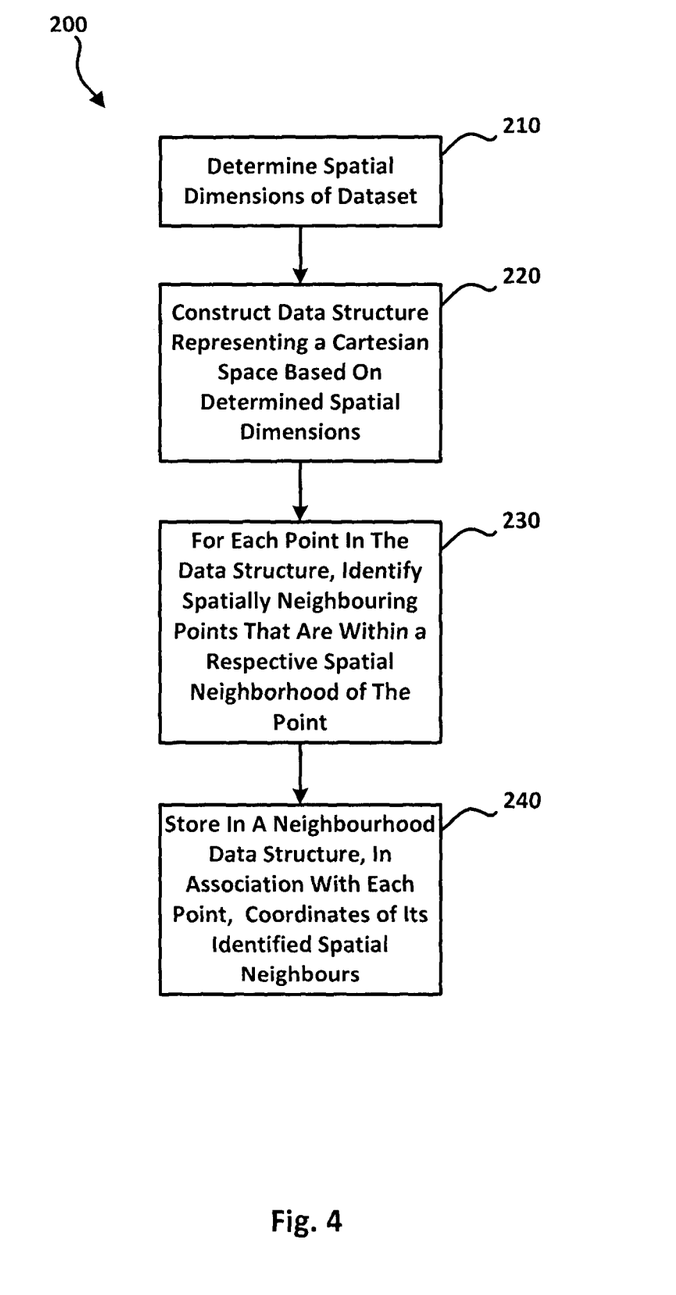
FIG. 4 is a flowchart depicting in further detail steps for determining spatially neighbouring points within a neighbourhood in a physical space for each point.

FIG. 4 is a flowchart depicting in further detail steps for determining spatially neighbouring points within a neighbourhood in a 3D volume for each point (step 200). In this embodiment, the spatial dimensions of the three-dimensional volume being assessed is determined based on the dataset (step 210). In this embodiment, the dataset is processed to calculate the range of each of the spatial dimensions x, y and z. Alternatively, the spatial resolution may be specified explicitly in the dataset and simply accessed, or fixed in a given implementation.

With the spatial resolution of the dataset having been determined, a three-dimensional data structure representing a three-dimensional Cartesian space is constructed based on the determined spatial dimensions (step 220). In this embodiment, the constructed three-dimensional Cartesian space has x, y and z dimensions that are the same as the three-dimensional volume from which the dataset of multidimensional signals has been captured. However, in an alternative embodiment, the spatial resolution of the Cartesian space may be established to be different, and does not need to be derived from or based on the dataset itself. That is, one does not require an actual dataset of multidimensional signals to establish spatial dimensions and resolution of the three-dimensional Cartesian space, nor to establish the spatially neighbouring points as described herein.

Spatially neighbouring points are identified for each non-zero point (i.e., the points corresponding to points in the brain in the three-dimensional volume being assessed as opposed to points outside of the brain in the three-dimensional volume) in the three-dimensional Cartesian space, by identifying those neighbouring points that are within a respective spatial neighbourhood in the three-dimensional Cartesian space from the point (step 230). In this embodiment, the spatial neighbourhood of each point is a spherical subvolume centred at the point having a predetermined radius r. In this way, the size of the spherical subvolume is defined by r, such that spatially-adjacent neighbouring points are those points within a Euclidean distance r from the point.

In particular, the point $(x_i, y_i, z_i)$ of each voxel $i \in \{1, \ldots, V\}$ in X is prescribed an open set $N(i)$ of neighbour voxels at respective points (x, y, z) that are within an Euclidean distance defined by spatial radius r in the three-dimensional Cartesian coordinate system using the Pythagorean distance metric, as represented as in Equation 2, below:

$$N(i) = \{(x,y,z) : \sqrt{(x-x_i)^2 + (y-y_i)^2 + (z-z_i)^2} \leq r\} \quad (2)$$

It will be understood that the number K of neighbouring voxels for each voxel is dependent on radius r, as represented in Equation 3, below:

$$K = (1+2r)^3 - 1 \quad (3)$$

With the open set of N(i) of neighbours having been identified for each point, the spatial locations (x, y, z) of the neighbours for each point are stored in a neighbourhood data structure in association with the point. In this embodiment, the locations are stored in the neighbourhood data structure sorted according to their spatial proximity to the point in association with which they are stored, ie. from closest neighbour to farthest neighbour. In this embodiment, the neighbourhood data structure is a two-dimensional matrix where the first dimension represents spatial locations of points for voxels $i \in \{1, \ldots, V\}$ and the second dimension stores as its elements the (x, y, z) locations of the spatially neighbouring points. The order is such that element one for a given point stores the location of its closest neighbouring point, element two stores the location of its second closest neighbouring point, element three stores the location of its third closest neighbouring point, and so forth until element K stores the location of its most distant neighbouring point.

The neighbourhood data structure, having been populated as described above for each spatial, non-zero point in the three-dimensional data structure representing the three-dimensional Cartesian space, is used for subsequent local linear embedding (LLE) processing on the dataset so that reconstruction weights for the signal at each point are established using signals at spatially neighbouring points that are within a spatial neighbourhood of the point in the three-dimensional volume. That is, since spatially neighbouring points are selected as described above, no further neighbourhood selection step for LLE is required in order to output a reconstructed dataset that may reveal underlying patterns that may be useful during subsequent processing, clinical diagnosis and so forth.

Each subject's dataset of multidimensional signals (in this embodiment fMRI signals) may be represented as a four-dimensional array X, as represented in Equation 4, below:

$$X \in \Re^{L \times W \times H \times T} \quad (4)$$

X has V=LWH T-dimensional fMRI signal waveforms represented as in Equation 5, below:

$$x_i \in \Re^T \quad (5)$$

for:
$i = 1, \ldots, V$

The processing is conducted on the assumption that a d-dimensional reconstruction z exists for every point's signal waveform for every subject's dataset. Such a reconstruction z for every voxel waveform x may be represented as in Equations 6 and 7, below:

$$z \in \Re^d \quad (6)$$

$$x \in \Re^T \quad (7)$$

The implementation of LLE, according to this embodiment, reconstructs X by first linearizing the spatial indices of the dataset to produce a two-dimensional array X, as represented in Equation 8, below, and ultimately to re-shape a resulting two-dimensional reconstruction array Z as represented in Equation 9, below, into a four-dimensional array as represented in Equation 10, below:

$$X \in \Re^{V \times T} \quad (8)$$

$$Z \in \Re^{B \times d} \quad (9)$$

$$Z \in \Re^{L \times W \times H \times d} \quad (10)$$

According to this embodiment, LLE reconstructs X by characterizing every voxel as a black body. This is done by undertaking a process that seeks to minimize the reconstruction cost of its fMRI signal waveform $x_i$ in terms of its spatially-adjacent neighbours. This minimization may be represented as in Equations 11 and 12, below:

$$\min \left\| x_i - \sum_{j \in N(i)} w_{i,j} x_j \right\|_2^2 \quad (11)$$

such that:

$$\sum_{j \in N(i)} w_{i,j} = 1 \quad (12)$$

As set forth above, N(i) is the open set of spatial neighbours, and $w_i = [w_{i,1}, \ldots w_{i,K}] \in R^K$ are the reconstruction weights for the K spatial neighbours that reflect the spatial pattern of the absorbed electromagnetic radiation at the spatial location of voxel i.

Figure 5:
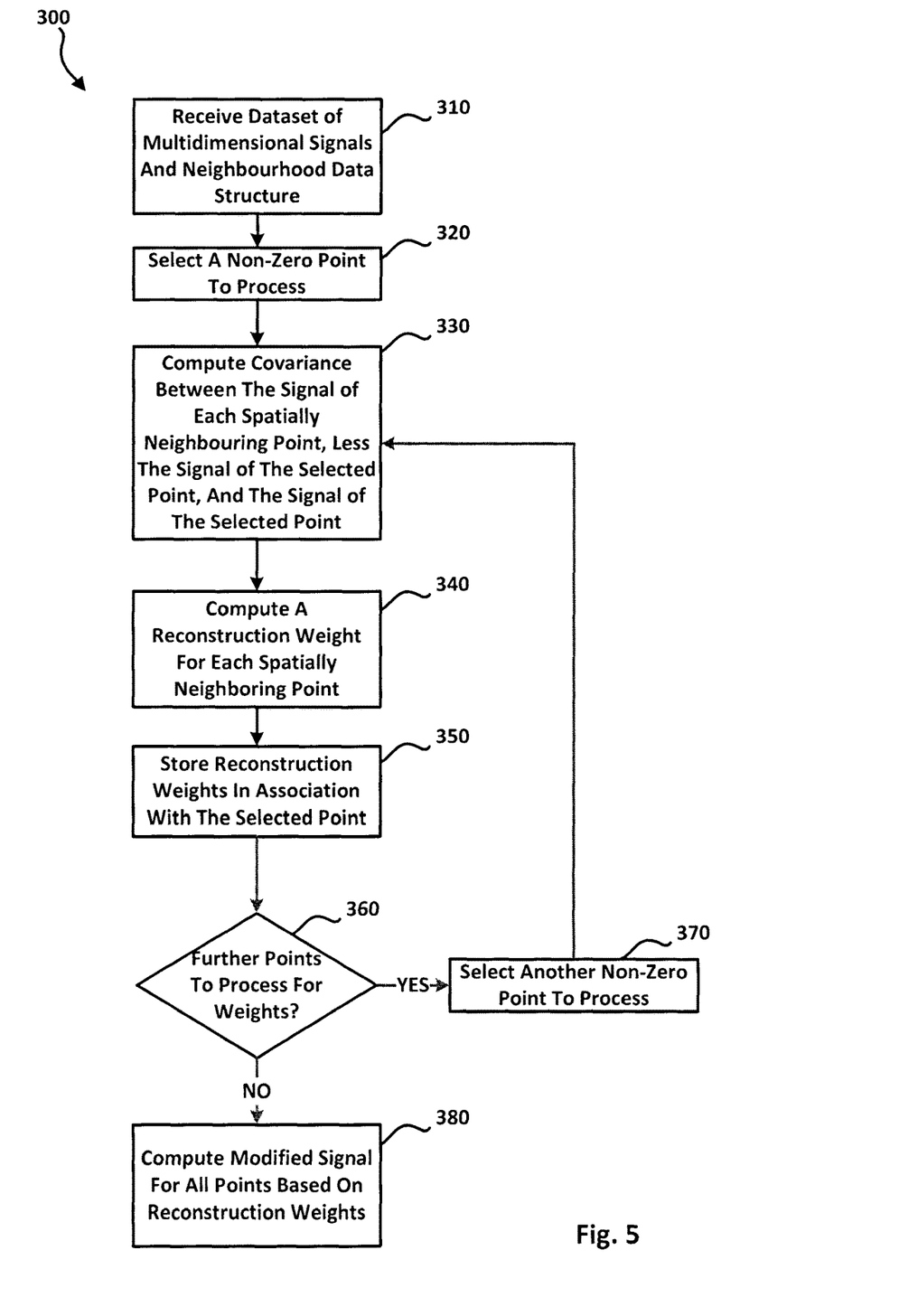
FIG. 5 is a flowchart depicting in further detail steps for reconstructing each point's signal based on the signals of its spatially neighbouring points.

FIG. 5 is a flowchart depicting in further detail steps for, with the neighbourhood data structure having been populated, creating a modified signal for each point based on the signals of respective spatially neighbouring points (step 300), according to this embodiment. The dataset and the neighbourhood data structure are received (step 310) and a first non-zero point is selected for processing (step 320). The covariance between the signal of each spatially neighbouring point, less the signal of the selected point, and the signal of the selected point, is then computed (step 330). In particular, to determine the black body at the selected point, the signal of the point is first subtracted from the signals of its neighbours $j \in N(i)$. This reflects the intuition that the electromagnetic radiation is absorbed at this point, and establishes an origin, or axis for the point, as depicted by the zero line in FIG. 1B.

A local Hilbert space $C_i$ is then computed as represented in Equation 13, below:

$$C_i = [(x_j - x_i), \ldots (x_{j+k} - x_i)]^T [(x_j - x_i), \ldots (x_{j+k} - x_i)] + \varepsilon_K \quad (13)$$

In Equation 13, $\varepsilon_K$ is a non-negative regularization term that conditions the Hilbert space $C_i$ to be positive definite. That is, this term simply adds a positive multiple down the diagonal of the matrix $C_i$. Based on $C_i$, a reconstruction weight for each spatially neighbouring point j is computed (step 340) by finding the unique minimum norm solution to the constrained local least squares problem that is defined by Equation 14, below:

$$C_i w_i = 1_K \quad (14)$$

where:

$1_K \in R^K$ is a vector of ones.

Because $C_i$ is a square-integrable space (known as a Lebesgue space or $l^2$), defined on a Cartesian space with the Pythagorean distance metric, the reconstruction weights $w_i$ are the resulting (local) Lebesgue measures containing the shift, rotation and translation-invariant geometric structure of the spatially-local contours of the space-filling curve that represents the local electric charge over time of selected point i. The constraint defined in Equation 14 ensures that the area between the selected point and the contour is 1 in each of the |N(i)| directions. The reconstruction weights $w_i$ are stored in association with the selected point i (step 350).

In the event that it is determined that there are further (non-zero) spatial points to process (step 360), another spatial point is selected (step 370) and the process continues from step 330 with the newly-selected spatial point. On the other hand, should it be determined at step 360 that there are no further spatial points to process as has been described above, a modified signal for each spatial point is computed based on its respective reconstruction weights (step 380).

During computing of modified signals based on respective construction weights, a modified signal for all points is computed using a constrained global least squares optimization based on the reconstruction weights, wherein the modified signals have unit covariance.

More particularly, the reconstruction weights w are used in a global optimization based on the Gauss Principle of Least Constraint, to calculate manifolds $z_i, \ldots z_V$, as represented in Equations 15 and 16, below:

$$\min_{z = [z_1, \ldots z_V]} \left\| z_i - \sum_{j \in N(i)} w_{i,j} z_j \right\|_2^2 \quad (15)$$

such that:

$$ZZ^T = I \quad (16)$$

In Equations 15 and 16, $Z \in R^{V \times d}$.

More particularly, a sparse matrix $W \in R^{V \times V}$ is constructed containing V voxels' K reconstruction weights. It is the case that $W_{i,j} \leftarrow w_{i,j} \neq 0 \leftrightarrow j \in N(i)$. Since neighbouring points are determined by Pythagorean distance, $j \in N(i) \leftrightarrow i \in N(j)$. The local linear embedding is done based on matrix W and not on the original inputs. As such, d-dimensional manifolds are constructed by computing the eigenvectors of the distance, or cost, matrix M as represented by Equation 17, below:

$$M = (I - W)^T (I - W) \quad (17)$$

It will be understood that, since no voxel is a neighbour of itself, matrix W will have zeroes down the diagonal. Subtracting W from the identity matrix I enforces the constraint that the weight vectors must sum to one. Each element of cost matrix M may be represented as in Equation 18, below:

$$M_{i,j} = \delta_{i,j} - w_{i,j} - w_{j,i} + \Sigma w_{i,k} w_{j,k} \quad (18)$$

where:

$\delta_{i,j} = 1 \Leftrightarrow i = j$ and is otherwise 0

Equation 18 and its constraint illustrates that the cost matrix M is also an adjacency matrix, where the off-diagonal elements characterize a highly non-linear relationship between voxels, and the diagonal elements enforce the constraint that the weights must sum to 1.

It is the case that the cost matrix M is sparse, symmetric and positive semidefinite. As such, it admits the eigen decomposition as represented in Equation 19, below:

$$M = Z \Lambda Z^T \quad (19)$$

In Equation 19, $\Lambda \in R^{(d+1) \times (d+1)}$ is the diagonal matrix containing the d+1 smallest eigenvalues of M, and $Z \in R^{V \times (d+1)}$ are the corresponding eigenvectors. The (d+1) eigenvector is the unit vector with equal components, which is discarded to enforce the constraint that the space-time manifolds have mean zero.

In order to avoid degenerate solutions, the local linear embedding requires that the manifolds be centered about the origin (see, for example, FIG. 1B) in both space and time, and that the manifolds have unit covariance. Centering the manifolds about the origin ensures that they are of the same scale. This is, to a degree, similar to what is known as BOLD-signal normalization, where the unit covariance constraint imposes the requirement that the reconstruction errors of the extracted manifolds are measured on the same scale.

Figure 6:
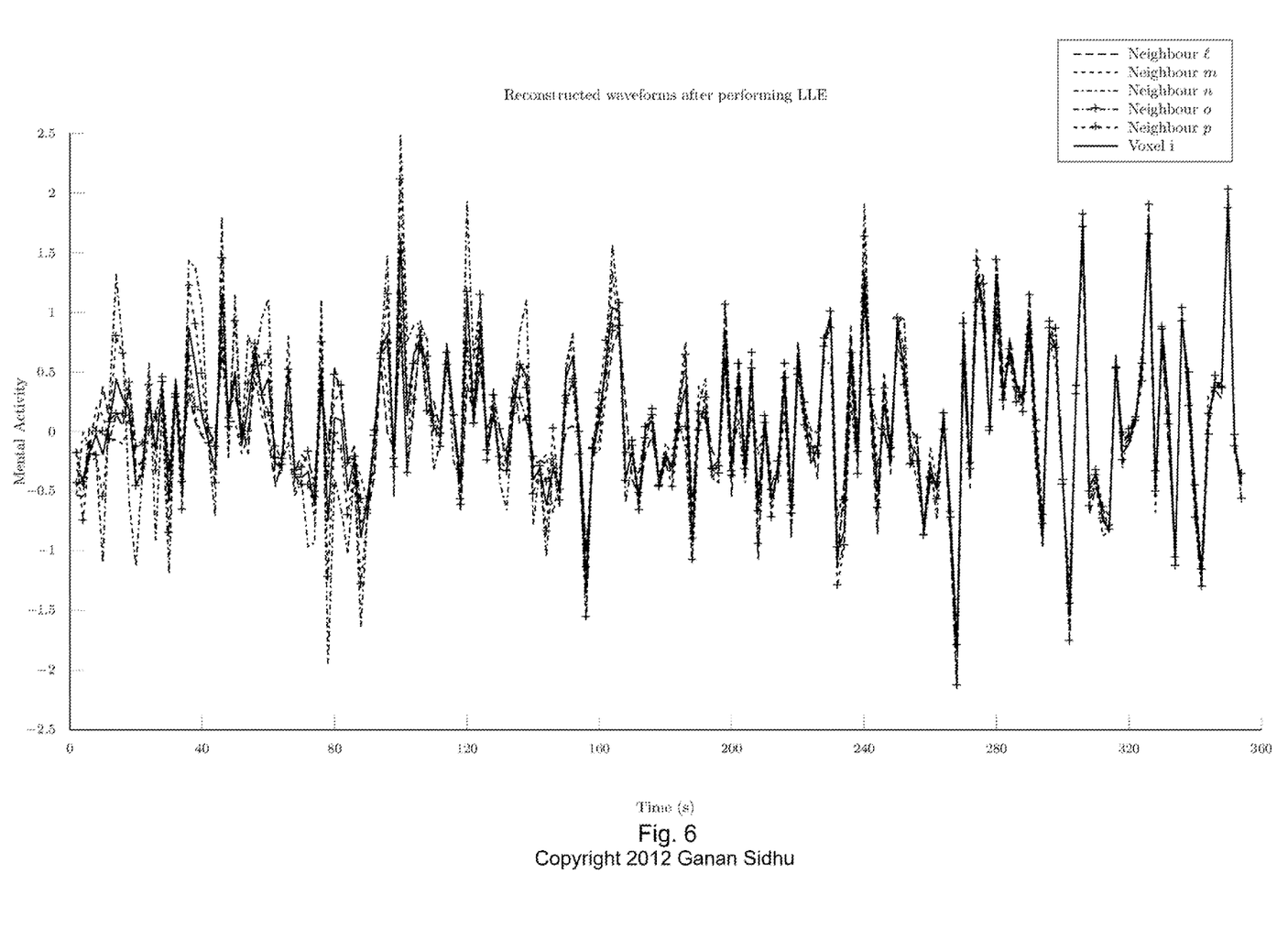
FIG. 6 is a plot of a reconstructed fMRI Z based in part on the raw fMRI signals depicted in the plot of FIG. 2.

FIG. 6 is a plot of a reconstructed fMRI Z based in part on the raw fMRI signals depicted in the plot of FIG. 2. As can be seen, the mathematical structures in the patterns of FIG. 2 are preserved in FIG. 6. That is, the hemodynamic patterns in the fMRI BOLD signals depicted in FIG. 2 are preserved during the reconstruction.

Figure 7:
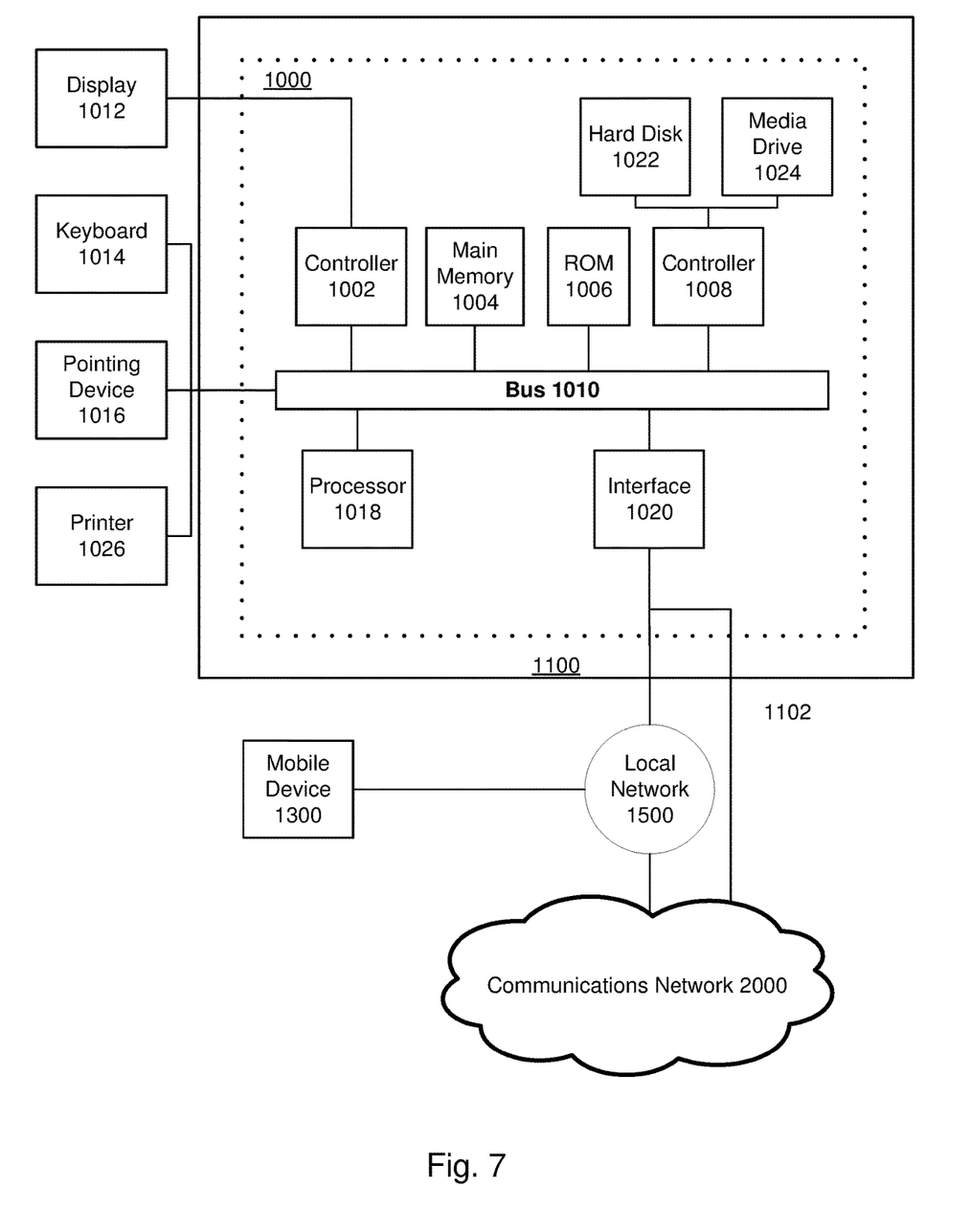
FIG. 7 is a schematic diagram of an aspect of the computing environment which may be used to implement one or more embodiments of the method described herein.

In this embodiment, process 90 is executed on a computing system 1000 such as that shown in FIG. 7. In an embodiment involving fMRI datasets, the computing system 1000 may be incorporated into an fMRI machine, a type of magnetic resonance imaging system 1100, or a downstream processing structure that receives a dataset 1101 of fMRI signals through input port 1102 in NIFTI or other suitable file format and can process the received dataset accordingly. The computing system processes the dataset 1101, and produces a magnetic resonance image for presentation to a user, e.g., at display 1012 or printer 1026.

In this embodiment, computing system 1000 includes a bus 1010 or other communication mechanism for communicating information, and a processor 1018 coupled with the bus 1010 for processing the information. The computing system 1000 also includes a main memory 1004, such as a random access memory (RAM) or other dynamic storage device (e.g., dynamic RAM (DRAM), static RAM (SRAM), and synchronous DRAM (SDRAM)), coupled to the bus 1010 for storing information and instructions to be executed by processor 1018. In addition, the main memory 1004 may be used for storing temporary variables or other intermediate information during the execution of instructions by the processor 1018. Processor 1018 may include memory structures such as registers for storing such temporary variables or other intermediate information during execution of instructions. The computing system 1000 further includes a read only memory (ROM) 1006 or other static storage device (e.g., programmable ROM (PROM), erasable PROM (EPROM), and electrically erasable PROM (EEPROM)) coupled to the bus 1010 for storing static information and instructions for the processor 1018.

The computing system 1000 also includes a disk controller 1008 coupled to the bus 1010 to control one or more storage devices for storing information and instructions, such as a magnetic hard disk 1022, and a removable media drive 1024 (e.g., floppy disk drive, read-only compact disc drive, read/write compact disc drive, compact disc jukebox, tape drive, and removable magneto-optical drive). The storage devices may be added to the computing system 1000 using an appropriate device interface (e.g., small computing system interface (SCSI), integrated device electronics (IDE), enhanced-IDE (E-IDE), direct memory access (DMA), or ultra-DMA).

The computing system 1000 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computing system 1000 may also include an output port, e.g., a display controller 1002 coupled to the bus 1010 to control a display 1012, such as a liquid crystal display (LCD) screen, for displaying information to a computer user. The computing system 1000 includes input devices, such as a keyboard 1014 and a pointing device 1016, for interacting with a computer user and providing information to the processor 1018. The pointing device 1016, for example, may be a mouse, a trackball, or a pointing stick for communicating direction information and command selections to the processor 1018 and for controlling cursor movement on the display 1012. In addition, a printer 1026 may provide printed listings of data stored and/or generated by the computing system 1000.

The computing system 1000 performs a portion or all of the processing steps of the invention in response to the processor 1018 executing one or more sequences of one or more instructions contained in a memory, such as the main memory 1004. Such instructions may be read into the main memory 1004 from another computer readable medium, such as a hard disk 1022 or a removable media drive 1024. One or more processors in a multi-processing arrangement may also be employed to execute the sequences of instructions contained in main memory 1004. In alternative embodiments, hard-wired circuitry may be used in place of or in combination with software instructions. Thus, embodiments are not limited to any specific combination of hardware circuitry and software.

As stated above, the computing system 1000 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computing system 1000, for driving a device or devices for implementing the invention, and for enabling the computing system 1000 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

A computer readable medium providing instructions to a processor 1018 may take many forms, including but not limited to, non-volatile media, volatile media, and transmission media. Non-volatile media includes, for example, optical, magnetic disks, and magneto-optical disks, such as the hard disk 1022 or the removable media drive 1024. Volatile media includes dynamic memory, such as the main memory 1004. Transmission media includes coaxial cables, copper wire and fibre optics, including the wires that make up the bus 1010. Transmission media also may also take the form of acoustic or light waves, such as those generated during radio wave and infrared data communications.

Various forms of computer readable media may be involved in carrying out one or more sequences of one or more instructions to processor 1018 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computing system 1000 may receive the data on the telephone line and use an infrared transmitter to convert the data to an infrared signal. An infrared detector coupled to the bus 1010 can receive the data carried in the infrared signal and place the data on the bus 1010. The bus 1010 carries the data to the main memory 1004, from which the processor 1018 retrieves and executes the instructions. The instructions received by the main memory 1004 may optionally be stored on storage device 1022 or 1024 either before or after execution by processor 1018.

The computing system 1000 also includes a communication interface 1020 coupled to the bus 1010. The communication interface 1020 provides a two-way data communication coupling to a network link that is connected to, for example, a local area network (LAN) 1500, or to another communications network 2000 such as the Internet. For example, the communication interface 1020 may be a network interface card to attach to any packet switched LAN. As another example, the communication interface 1020 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1020 sends and receives electrical, electromagnetic or optical signals that carry digital data streams representing various types of information.

The network link typically provides data communication through one or more networks to other data devices. For example, the network link may provide a connection to another computer through a local network 1500 (e.g., a LAN) or through equipment operated by a service provider, which provides communication services through a communications network 2000. The local network 1500 and the communications network 2000 use, for example, electrical, electromagnetic, or optical signals that carry digital data streams, and the associated physical layer (e.g., CAT 5 cable, coaxial cable, optical fibre, etc). The signals through the various networks and the signals on the network link and through the communication interface 1020, which carry the digital data to and from the computing system 1000 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computing system 1000 can transmit and receive data, including program code, through the network(s) 1500 and 2000, the network link and the communication interface 1020. Moreover, the network link may provide a connection through a LAN 1500 to a mobile device 1300 such as a personal digital assistant (PDA) laptop computer, or cellular telephone.

Alternative configurations of computing system 1000, such as those that are not interacted with directly by a human user through a graphical or text user interface, may be used to implement process 90.

Although embodiments have been described with reference to the drawings, those of skill in the art will appreciate that variations and modifications may be made without departing from the spirit, scope and purpose of the invention as defined by the appended claims.

For example, while the invention has been explained in detail using fMRI BOLD signals as multidimensional signals captured from points in a physical space that is a three-dimensional volume, the invention may be applicable to other kinds of multidimensional signals captured from points in other physical spaces by various detectors.

What is claimed is:

1. A method of generating a reduced-dimensionality representation of raw multidimensional signals, representing a plurality of separated nonlinear manifolds captured from a physical space by magnetic resonance imaging, and representing magnetic resonance image voxels, the method comprising:
receiving an array of the raw multidimensional signals generated by the magnetic resonance imaging and having a first dimensionality, as an input dataset;
determining Euclidean distances between elements within the array, based on a dimensionality of the received input dataset and a respective position of a respective element within the array;
linearizing spatial indices of the array to produce a linearized array of points having a second dimensionality;
for each respective point of the linearized array of points, using at least one automated processor;
based on the determined Euclidean distances of the respective point to other points of the linearized array of points, generating reconstruction weights for reconstructing the linearized array of points, using local linear embedding, at a minimized cost of reconstruction, from spatial neighbors of the respective point in the linearized array of points;
the spatial neighbors being selected based on the Euclidean distances and constrained to maintain spatial neighbor relationships;
storing the reconstruction weights in an output matrix having reduced dimensionality with respect to the raw multidimensional signals;
constructing modified signals having unit covariance from the stored reconstruction weights; and
producing a magnetic resonance image comprising the magnetic resonance image voxels, based on the constructed modified signals, wherein the plurality of nonlinear manifolds are separated.

2. The method of claim 1, wherein the input dataset is a dataset of raw functional Magnetic Resonance Imaging (fMRI) BOLD (Blood Oxygenation Level Dependent) signals.

3. The method of claim 1, wherein the linearized array of points has a spatial resolution that is the same as a spatial resolution of the input dataset and the reconstruction weights are used in a global optimization based on a Gauss Principle of Least Constraint for constructing the modified signals.

4. The method of claim 1, wherein the spatial neighbors of each respective point are within a spherical subvolume centered at each respective point and having a predetermined radius.

5. The method of claim 1, further comprising storing, in a neighborhood data structure, coordinates of the spatial neighbors of each respective point within the physical space, comprising storing the coordinates in an order corresponding to the Euclidean distance from each respective point.

6. The method of claim 1, wherein the generating step comprises:
for each of the spatial neighbors of a respective point:
computing covariance between:
a raw multidimensional signal captured at each respective point; and
a raw multidimensional signal captured at each of the spatial neighbors minus the raw multidimensional signal captured at each respective point; and
computing a reconstruction weight for each of the spatial neighbors based on a constrained local least-squares optimization of each covariance.

7. The method of claim 1, wherein the first dimensionality and the second dimensionality are different.

8. A non-transitory computer readable medium embodying instructions executable on an automated processor of a computing system for generating a modified representation of raw multidimensional signals representing a plurality of separated nonlinear manifolds captured from a physical space by magnetic resonance imaging, and representing magnetic resonance image voxels, the computer program comprising:
computer program code for receiving an array of the raw multidimensional signals representing the magnetic resonance image voxels generated by the magnetic resonance imaging and having a first dimensionality, as an input dataset;
computer program code for determining Euclidean distances between data points within the array, based on the first dimensionality of the received input dataset and a respective position of a respective element within the array;
computer program code for linearizing spatial indices of the array to produce a linearized array of points having a second dimensionality; and
computer program code for, for each respective point of the linearized array of points:
based on the Euclidean distances of each respective point to other points of the linearized array of points, generating reconstruction weights for reconstructing the linearized array of points, using local linear embedding, at a minimized cost of reconstruction, wherein the linearized array of points are from spatial neighbors of each respective point, the spatial neighbors being selected based on the Euclidean distances and constrained to maintain spatial neighbor relationships;
storing the reconstruction weights in an output matrix having reduced dimensionality with respect to the raw multidimensional signals;
constructing modified signals having unit covariance from the stored reconstruction weights; and
producing a magnetic resonance image comprising the magnetic resonance image voxels, based on the constructed modified signals.

9. The non-transitory computer readable medium of claim 8, wherein the input dataset is a dataset of raw functional Magnetic Resonance Imaging (fMRI) BOLD (Blood Oxygenation Level Dependent) signals.

10. The non-transitory computer readable medium of claim 8, wherein the linearized array if points has a spatial resolution that is the same as a spatial resolution of the input dataset and the reconstruction weights are used in a global optimization based on a Gauss Principle of Least Constraint for constructing the modified signals.

11. The non-transitory computer readable medium of claim 8, wherein the spatial neighbors of each respective point are within a spherical subvolume centered at each respective point and having a predetermined radius.

12. The non-transitory computer readable medium of claim 8, further comprising storing, in a neighborhood data structure, coordinates of the spatial neighbors of each respective point within the physical space, comprising storing the coordinates in an order corresponding to the Euclidean distance from each respective point.

13. The non-transitory computer readable medium of claim 8, wherein the generating step comprises:
for each of the spatial neighbors of a respective point:
computing covariance between:
a raw multidimensional signal captured at each respective point and
a raw multidimensional signal captured at each of the spatial neighbors minus the raw multidimensional signal captured at each respective point; and
computing a reconstruction weight for each of the spatial neighbors based on a constrained local least-squares optimization of each covariance.

14. The non-transitory computer-readable medium of claim 8, wherein the first dimensionality and the second dimensionality are different.

15. A computing system for generating a reduced-dimensionality reconstruction of raw multidimensional signals representing a plurality of separated nonlinear manifolds captured from a physical space by magnetic resonance imaging and representing magnetic resonance image voxels, comprising:
an input port configured to receive an input dataset comprising an array of the raw multidimensional signals representing the magnetic resonance image voxels generated by the magnetic resonance imaging and having a first dimensionality;
a memory;
at least one processor configured therewith to:
receive the input dataset as an array of the raw multidimensional signals generated by the magnetic resonance imaging and having a dimensionality;
determine Euclidean distances between datapoints within the array, based on a dimensionality of the received input dataset and a respective position of a respective element within the array;
linearize spatial indices of the array to produce a linearized array of points having a second dimensionality;
for each respective point of the linearized array of points:
based on the determined determine Euclidean distances of the respective point to other points of the linearized array of points, generate reconstruction weights, using local linear embedding, based on the linearized array of points, having a minimized a cost of reconstruction for reconstructing the linearized array of points from spatial neighbors of the respective point of the linearized array of points, selected based on the Euclidean distances and constrained to maintain spatial neighbor relationships;
store the reconstruction weights in an output matrix in the memory having reduced dimensionality with respect to the raw multidimensional signals;
construct modified signals having unit covariance, from the reconstruction weights stored in the memory and
produce a magnetic resonance image comprising the magnetic resonance image voxels based on the constructed modified signals, wherein the plurality of nonlinear manifolds are separated; and an output port configured to communicate the magnetic resonance image.

16. The computing system of claim 15, wherein the input dataset is a dataset of raw functional Magnetic Resonance Imaging (fMRI) BOLD (Blood Oxygenation Level Dependent) signals.

17. The computing system of claim 15, wherein the linearized array of points has a spatial resolution that is the same as a spatial resolution of the input dataset and the at least one automated processor is configured to use the reconstruction weights in a global optimization based on a Gauss Principle of Least Constraint for constructing the modified signals.

18. The computing system of claim 15, wherein the spatial neighbors of each respective point are within a spherical subvolume centered at each respective point and having a predetermined radius.

19. The computing system of claim 15, further comprising storing, in a neighborhood data structure, coordinates of the spatial neighbors of each respective point within the physical space, comprising storing the coordinates in an order corresponding to the Euclidean distance from each respective point.

20. The computing system of claim 15, wherein the at least one processor configured to generate is configured to:
for each of the spatial neighbors of a respective point:
compute covariance between:
a raw multidimensional signal captured at each respective point; and
a raw multidimensional signal captured at each of the spatial neighbors minus the raw multidimensional signal captured at each respective point; and
compute a reconstruction weight for each of the spatial neighbors based on a constrained local least-squares optimization of each covariance.

21. The computing system of claim 15, wherein the wherein the first dimensionality and the second dimensionality are different.

* * * * *